US00PP27882P2

(12) United States Plant Patent
Hansen

(10) Patent No.: US PP27,882 P2
(45) Date of Patent: Apr. 11, 2017

(54) ***DIANTHUS* PLANT NAMED 'MARASCHINO'**

(50) Latin Name: ***Dianthus* hybrid**
Varietal Denomination: Maraschino

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 14/757,107

(22) Filed: Nov. 19, 2015

(51) Int. Cl.
*A01H 5/02* (2006.01)

(52) U.S. Cl.
USPC ..... Plt./278

(58) Field of Classification Search
USPC ..... Plt./278, 283
CPC ..... A01H 5/0233
See application file for complete search history.

*Primary Examiner* — Kent L Bell

(57) ABSTRACT

A new and unique cultivar of perennial carnation or pinks plant, named *Dianthus* 'Maraschino' with completely double flowers of overlapping hot cherry-red petals and dark burgundy bands contrasts nicely with the dense, cool, icy, silver-blue compact foliage. 'Maraschino' tolerates high temperatures, resists center die-out of the clump and does not require vernalization to flower.

1 Drawing Sheet

Botanical denomination: *Dianthus* hybrid.
Cultivar designation: 'Maraschino'.

BACKGROUND OF THE INVENTION

The present invention relates to the new and distinct plant cultivar from the genus *Dianthus* or commonly referred to as carnation or pinks and given the cultivar name 'Maraschino'. This new cultivar name has been registered and approved by the International Cultivar Registration Authority for the genus *Dianthus* as a distinct name. The new plant was the result of an intentional cross in May 19, 2011 by the inventor between *Dianthus* 'Devon Xera' U.S. Plant Pat. No. 14,895 as the female or seed parent and 'Pomegranate Kiss' U.S. Plant Pat. No. 21,895 as the male or pollen parent. The seeds from the cross were collected on Jun. 21, 2011. The new hybrid was first isolated from among subsequent trials at a nursery in Zeeland, Mich. during the summer of 2012 as a single seedling and given the breeder number 11-167-01 during the evaluation process. *Dianthus* 'Maraschino' has been asexually propagated at the same nursery in Zeeland, Mich. using traditional shoot tip cutting procedures and found to reproduce plants that are identical and exhibit all the characteristics of the original plant.

No plants have been sold, either in this country or anywhere in the world, prior to the filing of this application, nor has any disclosure been made prior to the filing of this application with the exception of that which was within one year of the filing of this application and was derived directly or indirectly from the inventor.

SUMMARY OF THE INVENTION

The present invention has not been evaluated under all possible environmental conditions. The phenotype may vary with changes in the environment including: growing temperature, available sunlight, nutrients, water, etc. without a change in the genotype of the plant. The new plant is distinct from its parents and all other *Dianthus* known to the applicant in the following combined traits:

1. Full, completely double, fragrant flowers with overlapping petals of hot cherry-red;
2. Petals having a band of dark burgundy in the adaxial limb center;
3. High heat tolerance with no vernalization required for flower initiation;
4. Floriferous, vigorous, good reblooming and excellent habit; and
5. Compact, fine-textured, cool, icy, silver-blue foliage that remains in good shape through fall.

The nearest comparison cultivar known to the inventor is 'WP Passion' U.S. Plant Pat. No. 20,440. Comparing the 'WP Passion' with the new plant, 'Maraschino' has very similar flower color in the main petal portion, but 'WP Passion' lacks the dark burgundy band. 'WP Passion' also has smaller flowers without dentate petal apices, and the foliage is more green and less blue than 'Maraschino'. Compared to the female parent, 'Devon Xera', both plants have dark burgundy bands in the petals, but 'Devon Xera' has single flowers with only five petals per flower and 'Maraschino' is completely double with 20 to 28 petals. Foliage of 'Devon Xera' is similar in color and width to the new plant, but slightly longer in 'Maraschino'; and leaves of 'Devon Xera' are entire and 'Maraschino' is nearly microscopically serrulate. Compared to the male parent, 'Pomegranate Kiss', the new plant has hot cherry-red flower petals, while 'Pomegranate Kiss' has an irregular rose pink margin on the petals and is much shorter in overall flowering habit.

BRIEF DESCRIPTION OF THE DRAWINGS

The photographs of *Dianthus* 'Maraschino' demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
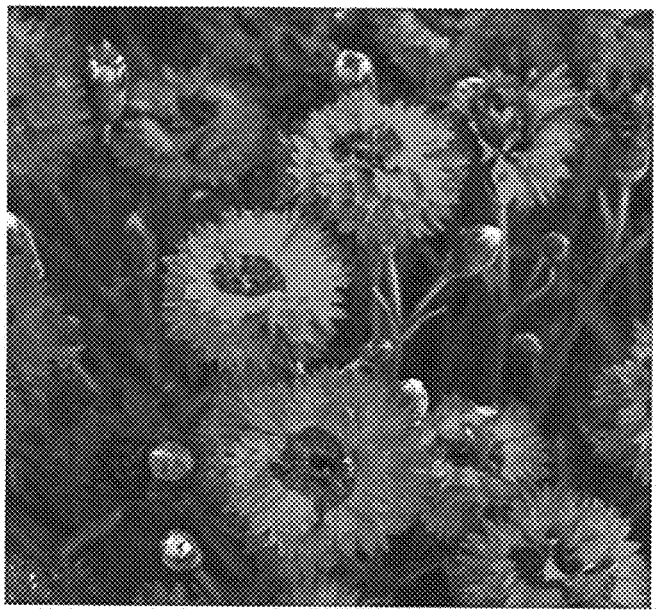
FIG. 1 shows a close-up of flowers.
Figure 2:
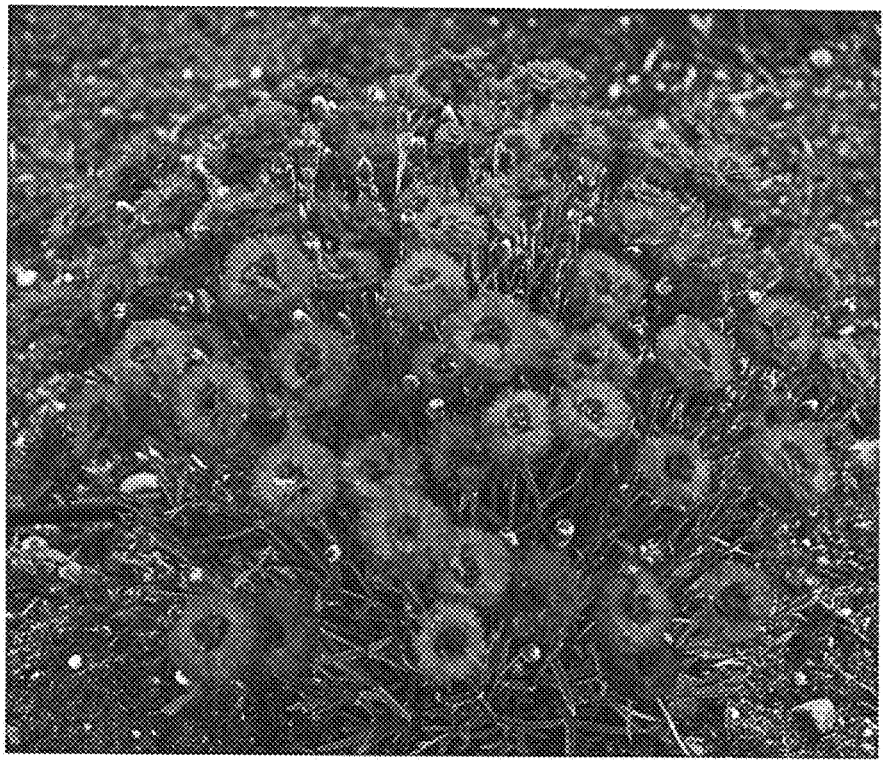
FIG. 2 shows the habit of the new plant in peak flower.

The following detailed description of the new plant is based on observations of two-year-old plants in full sun trial garden at a nursery in Zeeland, Mich. with supplemental watering, light additions of fertilizer and free of any plant growth regulators. All color usage is in accordance with the 2001 edition of The Royal Horticultural Colour Chart except where common dictionary terms are used.

Botanical classification: *Dianthus* hybrid.

Parentage: 'Devon Xera' U.S. Plant Pat. No. 14,895 as the female or seed parent, and 'Pomegranate Kiss' U.S. Plant Pat. No. 21,895 as the male or pollen parent.

Plant description:

*Habit*.—Caespitose, herbaceous, erect, rounded, dense, evergreen perennial; stems proximally branched, erect; height of foliage about 12.0 cm and 30.0 cm across; height in flower is about 25.0 cm.

*Root system*.—Fine, fibrous.

Foliage:

*Leaf type*.—Simple, linear, opposite, decussate, sessile, glabrous, glaucous on adaxial and abaxial surfaces; nearly microscopically serrulate, acute apex; base decurrent, fused in the basal 2.0 to 3.0 mm with opposite leaf; no fragrance detected.

*Leaf dimensions*.—About 5.0 to 6.5 cm long and about 3.5 to 4.0 mm wide; average about 6.0 cm long and about 4.0 mm wide.

*Leaf color*.—More green than RHS 122B and more blue than RHS 138A on adaxial and abaxial sides, with fused bases nearest RHS 145D.

*Venation*.—Finely reticulate.

*Vein color*.—Same as that of leaf adaxial and abaxial surfaces.

*Stems*.—Erect to slightly arching, terete, caulescent, herbaceous, glabrous, glaucous; about 70 stems per plant; proximally branching at 2 to 3 lower nodes; average internode length about 2.5 cm, closer at base and more spaced distally.

*Nodes*.—About 3.0 mm across; color nearest RHS N122B with tinting of RHS N187B.

*Stem size*.—About 28.0 cm long and about 2.5 mm wide at base.

*Stem color*.—Nearest RHS 122A with glaucous bloom and between RHS 136A and RHS 136B with bloom removed.

*Branches*.—About 25.0 cm, nearly as long as main stems; about 200 per plant.

Inflorescence:

*Type*.—Terminal, cymose, erect.

*Dimension*.—About 45.0 mm across and extending about 16.0 mm above calyx.

*Flowers per stem*.—Usually two, rarely three or one.

*Pedicel*.—Glaucous, glabrous, terete.

*Pedicel size*.—Average about 2.5 cm long and about 2 mm diameter.

*Pedicel color*.—Nearest RHS 122A with glaucous bloom and between RHS 136A and RHS 136B with bloom removed.

*Peduncle*.—Glaucous, glabrous, terete; about 22.0 cm to 25.0 cm long and 2.5 mm diameter at base.

*Peduncle color*.—Nearest RHS 122A with glaucous bloom and between RHS 136A and RHS 136B with bloom removed (more green than RHS 122B and more blue than RHS 138A).

Flowers:

*Type*.—Salverform, clawed, completely double, actinomophic.

*Flower bud*.—Rhomboid to terete; glaucous, glabrous; with rounded apex and acute base.

*Flower bud size one day prior to opening*.—About 2.5 cm long and 1.0 cm wide.

*Flower bud color*.—Glaucous, petals between RHS 59B and RHS 59C; sepals more green than RHS 122B and more blue than RHS 138A with areas of heavily tinted purple nearest N187A and RHS N 187B where exposed to high light intensity.

*Flower period*.—Beginning late May for about 3 weeks with a strong tendency to repeat in September for another three weeks if deadheaded.

*Fragrance*.—Light, sweet spicy, clove-like.

*Flower lasting quality*.—About five days on or off the plant.

*Petals*.—20 to 28 per flower; average about 23; each consisting of a rounded blade or limb and a claw; blade and claw combined are obovate; apex and margin deeply serrate with dentations to about 6.0 mm deep; adaxial surface bearded with minute hairs mostly congregated near center; distal limb portion bent outwardly above the calyx from about 90° to 120° angle from the claw; basal portion a claw tapering from limb to base of about 1.0 mm wide.

*Petal color*.—Adaxial distal limb between RHS 46A and RHS 53B; adaxial base of limb (ground) between RHS 59C and RHS 59D; abaxial limb nearest RHS 59C; adaxial and abaxial claw nearest RHS 150D in the center rib; adaxial and abaxial claw between the margin and the center nearest RHS 155D; adaxial and abaxial claw margin and the 5.0 mm of claw base translucent; broken band to nearly solid jagged bar about 5.0 mm wide near base of adaxial limb between RHS N186B and RHS N186A.

*Petal dimension*.—About 33.0 mm long including claw and limb with bend straightened; petal limb portion about 17.0 mm long and 22.0 mm wide; claws about 15.0 mm long and 1.0 mm wide at base and about 4.5 mm wide below limb.

*Androecium*.—About twelve typically, rudimentary. Filament: average about 8.0 mm long; color white, lighter than RHS 155D. Anther: rudimentary; average about 1.0 mm long and less than 0.5 mm across; usually flattened; color nearest RHS 161D. Pollen: not observed.

*Gynoecium*.—Style: split in two above ovary; puberulent on adaxial side, glabrous abaxial. Pistil: about 28.0 mm long and about 1.0 mm diameter; arcuate away from center; color lighter than RHS 155D about the basal 10.0 mm, quickly converting to nearest RHS N79B in about the distal 18.0 mm. Stigma: puberulent; about 1.0 cm long and 1.0 mm wide; color nearest RHS N79A. Ovary: superior to androecium and inferior to gynoecium, fusiform with rounded apex and truncate base; about 7.0 mm long and about 4.0 mm wide; color between RHS 145A and RHS 145B at distal end and between RHS 145 D and RHS 145 C at proximal end.

*Calyx*.—Glabrous, glaucous; consisting of five sepals with acute apex and fused base making up a five-toothed corolla tube fused in proximal 12.0 mm; about 17.0 mm long and 8.0 mm in diameter; entire margins.

*Calyx color*.—Adaxial nearest RHS N138D with glaucous bloom and nearest RHS 137C with bloom removed, also with dark blotches tinted with nearest RHS N186B and a lighter nearly transparent 0.5 mm margin above fusion of nearest RHS 160D; abaxial nearest RHS 146D with margins nearest RHS 160D.

*Bracteoles*.—Glabrous, glaucous acute apex, fused base, margin entire to nearly microscopically serrulate; consisting of four bracts in two pairs (two larger and two smaller); total size about 1.1 cm long and about 7.0 mm diameter; outer and larger bract about 1.5 mm across and about 11.0 mm long; inner and smaller bract dimensions about 4.0 mm across and about 7.0 mm long.

*Bracteole color*.—Same colors as calyx in both abaxial and adaxial.

Seed: Rare; only few have been observed; blackish brown darker than RHS 200A, shield-shaped, dorsiventrally compressed, about 3.0 mm across and 0.5 mm thick.

Capsule: Ovoid to cylindrical, opening by 4 teeth, about 2 cm long and 8.5 mm diameter, between RHS 164B and RHS 164A when dried.

Disease resistance: The new plant is resistance to center die out from fungus or high temperatures. The plant grows best with adequate moisture and well-drained soil, but is able to withstand high temperatures and some drought once established. Hardiness at least from USDA zone 4 through zone 9. Vernalization not required for flowering but 'Maraschino' does flower better and stronger following vernalization period.

I claim:

1. A new and distinct *Dianthus* plant named 'Maraschino' essentially as herein described and illustrated, suitable as a garden ornamental, potted plant and for cut flower arrangements.

* * * * *